United States Patent [19]

Gibbons

[11] 4,057,416

[45] Nov. 8, 1977

[54] 3-ALKYLTHIO-, 3-ALKYLSULFINYL-, AND 3-ALKYLSULFONYLISOTHIAZOLE DERIVATIVES AS HERBICIDES

[75] Inventor: Loren Kenneth Gibbons, Medina, N.Y.

[73] Assignee: FMC Corporation, Philadelphia, Pa.

[21] Appl. No.: 697,458

[22] Filed: June 18, 1976

[51] Int. Cl.$^2$ ............... C07D 275/02; A01N 9/12
[52] U.S. Cl. ............... 71/90; 260/306.8 A; 260/465.8 R; 260/551 S
[58] Field of Search ............... 260/306.8 A; 71/90

[56] References Cited

U.S. PATENT DOCUMENTS 3,118,901   1/1964   Hatchard ............... 260/306.8 A

Primary Examiner—R. Gallagher
Attorney, Agent, or Firm—Harrison H. Young, Jr.; Henry R. Ertelt

[57] ABSTRACT

A new class of herbicidal compounds consisting of 1-alkyl- and 1,1-dialkyl-3-(3,4-substituted-5-isothiazolyl) ureas and N-(3,4-substituted-5-isothiazolyl)-alkanamides in which the 3-substituent consists of alkylthio, alkylsulfinyl, and alkylsulfonyl, and the 4-substituent consists of cyano, and carbamoyl, exhibits preemergence and postemergence herbicidal activity, controlling effectively the growth of a wide spectrum of grassy and broad-leaved plant species. The synthesis of members of this class is described in detail, and the utility of representative compounds is exemplified.

19 Claims, No Drawings

3-ALKYLTHIO-, 3-ALKYLSULFINYL-, AND 3-ALKYLSULFONYLISOTHIAZOLE DERIVATIVES AS HERBICIDES

This invention describes novel herbicidal compounds, new herbicidal compositions, and new methods for preventing and destroying undesired plant growth by preemergence and postemergence application of said new and useful herbicidal compositions to the locus where control is desired. Effective control of the growth of a variety of grassy and broad-leaved plant species is obtained. At herbicidally effective levels of application, some compounds of the invention show selectivity favorable to corn and related species. The herbicidal compositions may be applied and utilized by commonly accepted methods.

Herbicidal isothiazole compounds having an alkyl group on the 3-position of the isothiazole ring; a cyano, carboxamide or alkoxycarbonyl group on the 4-position; and a substituted urea on the 5-position have been described in the patent literature. See, for example, Belgian Pat. No. 817,903 and published French application No. 2,132,191. It has been found that excellent herbicidal activity is obtained by having present on the 3-position, instead of an alkyl group, an alkylthio-, alkylsulfinyl, or alkylsulfonyl group. It has also been found that excellent herbicidal activity is obtained with compounds having such a 3-substituent when the compound has in the 5-position, instead of a substituted urea group, a substituted alkanoylamino group. Thus, in one aspect of the invention, novel herbicidal compounds contain an isothiazole ring having the following classes of substituents: on the 3-position, an alkylthio, alkylsulfinyl or alkylsulfonyl group; on the 4-position, a cyano, carboxamide or alkoxycarbonyl group; and on the 5-position, a substituted urea or alkanoylamino group.

One group of herbicidal compounds in accordance with this invention has the following structure (on which the numbering of the various positions of the isothiazole ring is also indicated):

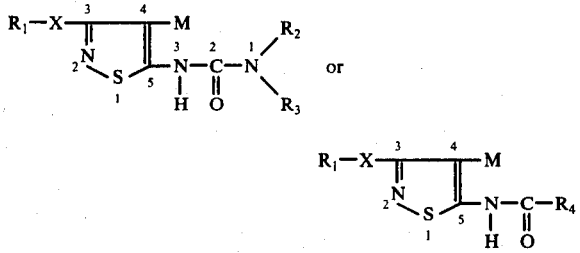

wherein $R_1$ is alkyl, alkenyl or cycloalkyl;
$R_2$ is alkyl, cycloalkyl or methoxy;
$R_3$ is alkyl or hydrogen, or $R_2$ and $R_3$ taken together form a divalent radical which may also contain a hetero atom;
$R_4$ is alkyl, alkenyl, haloalkyl or haloalkenyl;

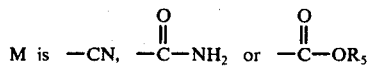

wherein $R_5$ is lower alkyl; and

X is —S—, —SO— or —$SO_2$—.

The alkyl, cycloalkyl and alkenyl groups preferably have less than 10 carbon atoms, more preferably they have less than 7 carbon atoms. Examples of alkyl groups are methyl, ethyl, propyl, isopropyl, isobutyl, sec-butyl, tert-butyl, 2-pentyl, and so forth. The alkylene groups preferably contain a total of four or five catenated atoms, no more than one of which is oxygen, sulfur or nitrogen. In the most preferred compounds, both $R_2$ and $R_4$ are lower alkyl, $R_3$ is H, M is carboxamide, and X is —S— or —$SO_2$—. In the descriptions which follow, all temperatures are in degrees centigrade. All reduced pressures not otherwise designated are pressures normally attainable using a water aspirator.

EXAMPLE I

1-Methyl-3-(4-cyano-3-(methylthio)-5-isothiazolyl)urea

A. Di(sodiomercapto)methylenemalononitrile

To a solution of 160 g of sodium hydroxide in 2300 ml of ethanol, stirred at 10°, was added dropwise, during 30 minutes, 132.2 g of malononitrile. The reaction mixture was stirred at 10° during an additional 30 minutes, then 152.3 g of carbon disulfide were added dropwise during one hour. The reaction mixture was allowed to warm to ambient temperature overnight. The slurry was cooled to 5°, and the solid was collected by filtration. The filter cake was washed with cold ethanol, and then with ether, to give a first crop of 258.6 g of di(sodiomercapto)methylenemalononitrile. A second crop of 132.9 g was obtained by concentration of the filtrate.

B. 2-cyano-3,3-bis(methylthio)propenenitrile

To a solution of 134.8 g of di(sodiomercapto)methylenemalononitrile in 600 ml of methanol were added dropwise 215.8 g of iodomethane during 15 minutes. The exothermic reaction caused the temperature to rise to 60°. The reaction mixture was heated under reflux for 16 hours. A 40-cm. fractionating column was employed in the removal of excess iodomethane and methanol by distillation. The residual solution was diluted with ether and water to give a slurry. The solid was collected by filtration. The water layer was extracted with ether several times. The combined extracts were dried over sodium sulfate and filtered. The filtrate was evaporated using a rotary evaporator to give a solid. The solid was combined with the filter cake above and recrystallized from 900 ml of methanol following clarification with charcoal to give 73.3 g of 2-cyano-3,3-bis(methylthio)-propenenitrile m.p. 80°–81°.

C. 3-Amino-2-cyano-3-(methylthio)propenenitrile

At 15°, 650 ml of ethanol was saturated with gaseous ammonia. Seventy-three and three-tenths grams of 2-cyano-3,3-bis(methylthio)propenenitrile were added portionwise during 10 minutes. The reaction mixture was heated to 78° during 15 minutes. The slurry was allowed to cool to ambient temperature, then cooled to 10°. The solid was collected by filtration and washed with cold ethanol to give, when dried, m.p. 228°–229° (Literature m.p. 229°–230°, R. Gompper and W. Topel, Ber. 95, 2871 (1902)).

D. 3-Amino-2-cyano-3-(methylthio)propenethioamide

A slurry of 48.8 g of 3-amino-2-cyano-3-(methylthio)-propenenitrile, 35.5 g of triethylamine, 50 ml of pyridine (previously dried over KOH) and 75 ml of dimethylformamide was heated to 65°. Gaseous hydrogen sulfide was added until the system became homogeneous. The reaction mixture was heated to 80°. The hydrogen sulfide addition was continued until comparative thinlayer chromatography indicated the reaction to be complete. The reaction mixture was heated at 80° for an additional 15 minutes and was poured into 1000 ml of ice-water.

The resultant slurry was stirred for 30 minutes. The solid was collected by filtration and washed with water to give, upon drying, 20.0 g of 3-amino-2-cyano-3-(methylthio)propenethioamide, m.p. 214°–215°.

E. 5-Amino-4-cyano-3-(methylthio)isothiazole

A slurry of 18.7 g of 3-amino-2-cyano-3-(methylthio)propenethioamide in 100 ml of ethanol was heated under reflux, as 14 ml (4.1 g) of 30% hydrogen peroxide were added dropwise. The exothermic reaction kept the system under reflux. The solution was heated under reflux for 30 minutes. The reaction mixture was allowed to cool to ambient temperature while it was stirred overnight. The white solid was collected by filtration to give 16.4 g of 5-amino-4-cyano-3-(methylthio)isothiazole; m.p. 188°–189°. The nmr spectrum was consistent with the assigned structure.

Analysis: Calc'd for $C_5H_5N_3S_2$: C 35.10; H 2.95; N 24.56; Found: C 35.23; H 2.85; N 24.59.

F. 1-Methyl-3-(4-cyano-3-(methylthio)-5-isothiazolyl)urea

A solution of 27.4 g of 5-amino-4-cyano-3-(methylthio)isothiazole, 9.7 g of methyl isocyanate, and 50 drops of dibutyltin diacetate in 150 ml of tetrahydrofuran was heated under reflux during 16 hours. Comparative thin-layer chromatography indicated the reaction to be 50% complete. An additional 10 ml of methyl isocyanate and 20 drops of dibutyltin diacetate were added and the heating continued for eight hours. Comparative thin-layer chromatography indicated that the reaction was still only 50% complete. An additional 10 g of methyl isocyanate were added to the reaction mixture, and the heating was continued overnight. The solid was isolated from the slurry by filtration to give a first crop of 1-methyl-3-(4-cyano-3-(methylthio)-5-isothiazolyl)urea, m.p. 250° (resolidified and m.p. 290°–292°). The filtrate was evaporated to give a tan solid. This solid was recrystallized from ethanol to give a second crop of product. The mother liquor was concentrated to give a third crop. The total yield was 33.4 g of 1-methyl-3-(4-cyano-3-(methylthio)-5-isothiazollyl)urea. Recrystallization from ethanol gave a solid, m.p. 248°–250°, resolidified, m.p. 286°. The nmr spectrum was consistent with the assigned structure.

Analysis: Calc'd for $C_7H_8N_4S_2O$: C 36.85; H 3.53; N 24.56; Found: C 37.15; H 3.74; N 24.80.

EXAMPLE II.

1-Methyl-3-(4-cyano-3-(methylsulfinyl)-5-isothiazolyl)urea

A solution of 1.14 g of 1-methyl-3-(4-cyano-3-(methylthio)-5-isothiazolyl)urea in 10 ml of acetic acid was heated to 90°, and 0.6 ml of 30% hydrogen peroxide were added dropwise. The heating was continued during 30 minutes. Comparative thin-layer chromatography indicated the reaction was near completion. An additional 5 drops of hydrogen peroxide were added and the heating was continued for 30 minutes. The reaction mixture was cooled to 5°, and 0.5 g of the solid 1-methyl-3-(4-cyano-3-(methylsulfinyl)-5-isothiazolyl)urea, m.p. 243° (decomposes), were collected by filtration. The nmr spectrum was consistent with the assigned structure.

Anaylsis: Calc'd for $C_7H_8N_4S_2O_2$: C 34.43; H 3.30; N 22.95; S 26.26; Found: C 34.12; H 3.29; N 23.03; S 26.48.

The reaction was repeated using 24.2 of 1-methyl-3-(4-cyano-3-(methylthio)-5-isothiazolyl)urea and 12 ml of 30% hydrogen peroxide in 175 ml of acetic acid to give 7.9 g of 1-methyl-3-(4-cyano-3-(methylsulfinyl)-5-isothiazolyl)urea, m.p. 241° (decomposes).

EXAMPLE III

1-Methyl-3-(4-carbamoyl-3-(methylsulfonyl)-5-isothiazolyl)urea

The filtrate from the second synthesis of 1-methyl-3-(4-cyano-3-(methylsulfinyl)-5-isothiazolyl)urea (Example II) was heated to 90° and to the mixture was added 15 ml of 30% hydrogen peroxide. The exothermic reaction increased the temperature to 110°. The mixture was maintained at 100° for one hour, then was cooled to 5°. The precipitate was collected and, after drying, examined by thin-layer chromatography when it was found to consist of two components. The solid was redissolved in acetic acid and treated with excess 30% hydrogen peroxide at 100° for 10 minutes, then cooled to −5°. The solid was isolated to give 9.6 g of 1-methyl-3-(4-carbamoyl-3-(methylsulfonyl)-5-isothiazolyl)urea, m.p. 227°–228°, which was found by thin-layer chromatography to be free of the previously observed second component. The nmr spectrum was consistent with the assigned structure.

Analysis: Calc'd for $C_7H_{10}N_4S_2O_4$: C 30.22; H 3.62; N 20.14; S 23.05; Found: C 30.72; H 3.64; N 19.60; S 23.39.

EXAMPLE IV 1,1-Dimethyl-3-(4-cyano-3-(methylthio)-5-isothiazolyl)urea

A. Phenyl (4-cyano-3-(methylthio)-5-isothiazolyl)carbamate

A solution of 14.4 g of 5-amino-4-cyano-3-(methylthio)isothiazole, 15.7 g of phenyl chloroformate in 50 ml of toluene was heated at 100° during 16 hours while gaseous nitrogen bubbled through. An additional 24.0 g of phenyl chloroformate were added to the reaction mixture and the heating at 100° was continued for 24 hours. Comparative thin-layer chromatography indicated that a small amount of 5-aminoisothiazole remained unreacted. The solution was allowed to cool to ambient temperature, then was filtered. The filter cake was slurried with hot ethanol to give: a solid (a) not dissolved in hot ethanol; a solid (b) obtained by cooling the ethanol solution; a solid (c) obtained by concentration of the filtrate; a solid (d) obtained by evaporation of the filtrate to dryness. Comparative thin-layer chromatography indicated that solids (a), (b), and (c) were the same and that they were pure. Solid (d) was unreacted starting aminoisothiazole.

The solids (a), (b), and (c) were combined and recrystallized from ethanol, dimethylformamide and water to give 19.0 g of phenyl (4-cyano-3-(methylthio)-5-isothiazolyl)carbamate, m.p. 244°–245°. The nmr spectrum was consistent with the assigned structure.

Analysis: Calc'd for $C_{12}H_9N_3O_2S_2$: C 49.49; H 3.12; N 14.43; Found: C 49.27; H 3.06; N 14.27.

B. 1,1-Dimethyl-3-(4-cyano-3-(methylthio)-5-isothiazolyl)urea

In a pressure bottle were placed 14.7 g of phenyl (4-cyano-3-(methylthio)-5-isothiazolyl)carbamate and 50 ml of dimethylformamide. The solution was cooled to 0° and 6.6 ml (4.43 g) of dimethylamine (previously condensed into a graduated addition funnel) were added. The pressure bottle was sealed and the reaction mixture heated at 80° for four hours. The pressure bottle and the reaction mixture were cooled to −5° and the bottle opened. Evaporation of the reaction mixture at 100° gave a solid which was recrystallized from methanol-ethanol, then dimethylformamide to give a first crop of 7.0 g, m.p. 246°-247°. Concentration of the mother liquor gave a second crop of 1.9 g of product, m.p. 246°-247°. Further concentration at 60°, using the rotary evaporator gave a third crop of 2.8 g of product; m.p. 246°-247°. The crops were combined to give a total yield of 11.6 g of 1,1-dimethyl-3-(4-cyano-3-(methylthio)-5-isothiazolyl)urea. The nmr spectrum was consistent with the assigned structure.

Analysis: Calc'd for $C_8H_{10}N_4OS_2$: C 39.67; H 4.16; N 23.13; Found: C 39.41; H 3.19; N 23.42.

EXAMPLE V 1,1-Dimethyl-3-(4-cyano-3-(methylsulfinyl)-5-isothiazolyl)urea

In the manner of Example II, 7.9 g of 1,1-dimethyl-3-(4-cyano-3-(methylthio)-5-isothiazolyl)urea was oxidized with 3.7 ml of 30% hydrogen peroxide to give 7.0 g of 1,1-dimethyl-3-(4-cyano-3-(methylsulfinyl)-5-isothiazolyl)urea, m.p. 178°-179°. The nmr spectrum was consistent with the assigned structure.

Analysis: Calc'd for $C_8H_{10}N_4O_2S_2$: C 37.22; H 3.90; N 21.70; S 24.83; Found: C 37.40; H 3.86; N 21.92; S 24.78.

EXAMPLE VI 1,1-Dimethyl-3-(4cyano-3-(methylsulfonyl)-5-isothiazolyl)urea

A suspension of 4.0 g of 3-(4-cyano-3-(methylsulfinyl)-5-isothiazolyl)urea in 30 ml of acetic acid was heated to 90° (solid dissolved during the heating period) and to the solution was added 2.8 ml of 30% hydrogen peroxide. The mixture was held at 90° for one hour. An additional small amount of 30% hydrogen peroxide was added and the temperature increased to 100° for 0.5 hour. The mixture was cooled to —5°, then mixed with 40 ml of ice-water. The solid was isolated on a filter, washed with cold water and dried to give 3.5 g of 1,1-dimethyl-3-(4-cyano-3-(methylsulfonyl)-5-isothiazolyl)urea, m.p. 243°-244°. The nmr spectrum was consistent with the assigned structure.

Analysis: Calc'd for $C_8H_{10}N_4O_3S_2$: C 35.04; H 3.68; N 20.43; S 23.39; Found: C 35.18; H 3.83; N 20.67; S 23.58.

EXAMPLE VII

1-Methyl-3-(4-carbamoyl-3-(methylthio)-5-isothiazolyl)urea

A solution of 5.0 g of 1-methyl-3-(4-cyano-3-)methylthio)-5-isothiazolyl)urea in 10 ml of concentrated sulfuric acid was heated at 100° during 30 minutes. The reaction mixture was poured into 100 ml of ice-water. The white solid precipitate was collected by filtration and recrystallized from 750 ml of 1:1 ethanol:methanol to give a first crop of 3.6 g of solid, m.p. 241°-242°, resolidified m.p. 285° (decomposes). A second crop of 0.9 g was obtained by the concentration of the mother liquor to 100 ml. The total yield of 1-methyl-3-(4-carbamoyl-3-(methylthio)-5-isothiazolyl)urea was 4.5 g. The nmr spectrum was consistent with the assigned structure.

Analysis: Calc'd for $C_7H_{10}N_4S_2O_2$: C 34.15; H 4.09; N 22.26; S 26.05; Found: C 34.40; H 4.16; N 21.97; S 26.42.

EXAMPLE VIII

1-Methyl-3-(4-carbamoyl-3-(methylsulfinyl)-5-isothiazolyl)urea

A mixture of 4.9 g of 1-methyl-3-(4-carbamoyl-3-(methylthio)-5-isothiazolyl)urea and 20 ml of acetic acid was heated to 95° and to the hot mixture was added dropwise 2.2 ml of 30% hydrogen peroxide. The mixture became homogeneous, but solid began to appear again after a few minutes. The mixture was maintained at 95° for two hours and then 9 drops of 30% hydrogen peroxide were added. After heating was continued an additional hour, thin-layer chromatographic analysis indicated that the reaction was completed. The mixture was cooled to -5°; the solid was isolated, washed with cold water and dried to give 4.7 g of 1-methyl-3-(4-carbamoyl-3-(methylsulfinyl)-5-isothiazolyl)urea; m.p. above 355°. The nmr spectrum was consistent with the assigned structure.

Analysis: Calc'd for $C_7H_{10}N_4S_2O_3$: C 32.07; H 3.84; N 21.37; S 24.46; Found: C 32.22; H 3.89; N 21.45; S 24.34.

EXAMPLE IX

1-Methyl-3-(4-cyano-3-(methylsulfonyl)-5-isothiazolyl)urea

To a slurry of 1.14 g of 1-methyl-3-(4-cyano-3-(methylthio)-5-isothiazolyl)urea in 5 ml of acetic acid at 90° was added 1.13 ml of 30% hydrogen peroxide. Exothermic reaction increased the temperature to 95° and the mixture became homogeneous, then solid slowly reappeared as heating continued eventually requiring addition of 5 ml of acetic acid to maintain fluidity. After 1 hour at 90°, the mixture was cooled to -5° and the solid isolated to give 1.2 g of 1-methyl-3-(4-cyano-3-((methylsulfonyl)-5-isothiazolyl)urea, m.p. 265°-6° (decomposes). Analysis by thin-layer chromatography indicated a trace of the corresponding methylsulfinyl compound, but repeated attempts at recrystallization did not eliminate it. The nmr spectrum was consistent with the assigned structure.

Analysis: Calc'd for $C_7H_8N_4S_2O_3$: C 32.32; H 3.10; N 21.54; Found: C 32.60; H 3.20; N 21.83.

An additional 4.6 g of 1-methyl-3-(4-cyano-3-(methylthio) -5-isothiazolyl)urea was treated at 100° with 5.7 ml of 30% hydrogen peroxide to give 4.6 g of 1-methyl-3-(4-cyano-3-(methylsulfonyl)-5-isothiazolyl)- urea, m.p. 275°.

EXAMPLE X (A)

N-(4-Cyano-3-(methylthio)-5-isothiazolyl)-2,2-dimethylpropionamide and (B)

N-(4-Carbamoyl-3-(methylthio)-5-isothiazolyl)-2,2-dimethylpropionamide

A slurry of 13.0 g of 5-amino-4-cyano-3-(methylthio)-isothiazole and 15.6 g of 2,2-dimethylpropionic anhydride was heated at 100° for 0.5 hour. An additional 15.6 g of anhydride were added and the mixture heated at 100° for another 0.5 hour. Thin-layer chromatographic analysis indicated no reaction. Anhydrous hydrogen chloride was passed through the mixture while the temperature was maintained at 100°. After 0.5 hour, thin-layer chromatography indicated reaction to be about 10% complete. An additional 10 ml of 2,2-dimethylpropionic anhydride was added and hydrogen chloride addition was continued for 15 minutes. After the mixture was heated at 100° for 16 hours, thin-layer chromatography indicated about 50% reaction.

Ten ml of 2,2-dimethylpropionyl chloride was added and the mixture was heated at 165° for one hour. Gaseous hydrogen chloride was again introduced for 45 minutes and an additional 7.5 g of 2,2-dimethylpropionic anhydride was added as heating at 165° was continued for three hours. 2,2-Dimethylpropionic acid was removed by distillation and the residual solid was triturated with pentane. The solid (about 18.5 g) was treated with 10% aqueous sodium hydroxide and the mixture filtered. The filtrate was treated with decolorizing charcoal and adjusted to ph 8 with carbon dioxide. The precipitate was collected and the filtrate further treated with carbon dioxide. The precipitates were combined and air-dried.

The dried solid was placed on a silica gel column (about 400 g) and the column treated with cyclohexane containing progressively greater amounts of ethyl acetate. The progress of the elution was followed by thin-layer chromatography. The fractions collected were 80 ml each.

Fraction 1 was discarded.

Fraction 2 - 7 (1:1 cyclohexane:ethyl acetate) were combined and evaporated to give a solid which was recrystallized from ethanol to give 3.3 g of pure N-(4-cyano-3-(methylthio)-5-isothiazolyl)-2,2-dimethyl- propionamide, m.p. 177°–178°. The nmr spectrum was consistent with the assigned structure.

Analysis: Calc'd for $C_{10}H_{13}N_3S_2O$: C 47.06; H 5.13; N 16.46; S 25.08; Found: C 47.30; H 5.40; N 16.67; S 25.30.

Fraction 8 was discarded.

Fractions 9 - 15 (also 1:1 cyclohexane:ethyl acetate) were combined and evaporated to give a solid which was recrystallized from ethanol to give 3.7 g of pure N-(4-carbamoyl-3-(methylthio)-5-isothiazolyl)-2,2-dimethylpropionamide, m.p. 142°–143°. The nmr and ir spectra were consistent with the assigned structure.

Analysis: Calc'd for $C_{10}H_{15}N_3S_2O_2$: C 43.96; H 5.53; N 15.38; S 23.42; Found: C 43.97; H 5.72; N 15.63; S 23.26.

EXAMPLE XI

1-Methyl-3-(4-cyano-3-(ethylthio)-5-isothiazolyl)urea

A. 2-cyano-3,3-bio(ethylthio)propenenitrile

A solution of 2.5 moles of di(sodiomercapto)- methylenemalononitrile in ethanol was prepared by reacting 165.2 g of malononitrile, 200 g of sodium hydroxide and 190.4 g of carbon disulfide in 2250 ml of ethanol as described in Example I A. To this solution at ambient temperature was added dropwise during 15 minutes 770.9 g diethyl sulfate. During the addition the heat of reaction caused the reaction mixture temperature to rise to 53°. Upon complete addition the reaction mixture was stirred for 45 minutes, then heated under reflux for 30 minutes. With continued heating 1.5 liters of ethanol were removed by distillation; then the remainder removed by vacuum distillation. The residue was cooled, and 3 liters of ice-water was added. The mixture was cooled in an ice-bath during one hour, then chilled to -10°. The slurry was filtered and the solid washed with 1200 ml of pentane to give 378 g of 2-cyano-3,3-bis(ethylthio)propenenitrile B. 3-Amino-2-cyano-3-(ethylthio)propenenitrile Into 2.0 liters of ethanol, previously saturated with ammonia, was added 378 g of 2-cyano-3,3-bis(ethylthio)propenenitrile. The mildly exothermic reaction warmed the mixture to 38°. The mixture was stirred at ambient temperature for 0.5 hour, then heated under reflux (ca 55°) for 1.0 hour. The mixture was concentrated by distillation of about one liter of solvent. To the mixture was added 1.5 liters of ice-water and the mixture was cooled in an ice-bath. The yellow solid was isolated and dried to give 223 g of 3-amino-2-cyano-3-(ethylthio)propenenitrile, m.p. 180°–182°. The nmr spectrum was consistent with the assigned structure.

Analysis: Calc'd for $C_6H_7N_3S$: C 47.04; H 4.61; N 27.43; Found: C 46.95; H 4.69; N 27.38.

C. 3-Amino-2-cyano-3-(ethylthio)propenethioamide

A mixture of 220 g of 3-amino-2-cyano-3-(ethylthio)propenenitrile, 145.3 g of triethylamine in 775 ml of pyridine was heated to 25°. Into this was bubbled 127 g of hydrogen sulfide gas during 3.5 hours. During this time the exothermic reaction caused the reaction mixture temperature to rise to 50°. After complete addition, the reaction mixture was stirred during 16 hours, while the reaction mixture temperature was allowed to return to ambient temperature. Pyridine was removed by distillation and the residual semisolid was slurried with 1500 ml of cold water. The solid was collected by filtration and recrystallized from 5000 ml of ethanol to give, in three crops, 94.2 g of 3-amino-2-cyano-3-(ethylthio)propenethioamide; m.p. 200°–201°. The nmr spectrum was consistent with the assigned structure.

Analysis: Calc'd for $C_6H_9N_3S_2$: C 38.51; H 4.85; N 22.45; Found: C 38.74; H 4.71; N 22.63.

D. 5-Amino-4-cyano-3-(ethylthio)isothiazole

A slurry of 88.3 g of 3-amino-2-cyano-3-(ethylthio)propenethioamide in 800 ml of ethanol was treated with 55 ml of 30% hydrogen peroxide as described in Example I E and the mixture heated under reflux for 1.75 hours. The hot solution was filtered and concentrated to 500 ml. About 250 ml of cold water was added and the mixture allowed to stand overnight. The mixture was chilled to 5° and the solid isolated on a filter to give, after drying, 56.2 g of white solid, m.p. 122°–123°.

The filtrate was concentrated to about 200 ml and again chilled and filtered to obtain 27.2 g of pale yellow solid, m.p. 123°–124°. The nmr spectra indicated both solids to be essentially pure 5-amino-4-cyano-3-(ethylthio)isothiazole.

E. 1-Methyl-3-(4-cyano-3-(ethylthio)-5-isothiazolyl)urea

A solution of 35.0 g of 5-amino-4-cyano-3-(ethylthio)isothiazole, 11.9 g of methyl isocyanate, 50 drops of dibutyltin diacetate in 175 ml of dried tetrahydrofuran was heated under reflux during 15 hours. Thin-layer chromatographic analysis of the reaction mixture indicated the reaction was 50% complete. An additional 11 ml of methyl isocyanate and 10–15 drops of dibutyltin diacetate were added. The reaction mixture was heated with stirring for 2 days. Thin-layer chromatographic analysis of the reaction mixture indicated the reaction to be complete. The reaction mixture was cooled, and the solid collected by filtration. The filtrate was evaporated to give a second crop, which was recrystallized from ethanol/dimethylformamide. The total yield of pure 1-methyl-3-(4-cyano-3-(ethylthio)-5-isothiazolyl)urea was 37.6 g; m.p. 246° (phase change) — 263°. The nmr spectrum was consistent with the assigned structure.

Analysis: Calc'd for $C_8H_{10}N_4OS_2$: C 39.67; H 4.16; N 23.13; Found: C 40.02; H 4.24; N 23.36.

EXAMPLE XII

1,1-Dimethyl-3-(ethylthio)-5-isothiazolyl)urea

A. Phenyl (4-cyano-3-(ethylthio)-5-isothiazolyl)-carbamate

Under a nitrogen atmosphere, a mixture of 45.0 g of 5-amino-4-cyano-3-(ethylthio)isothiazole and 47.0 g of phenyl chloroformate in 175 ml of dried toluene was heated under reflux for 16 hours; thin-layer chromatography indicated the reaction to be complete. The reaction mixture was cooled to 10°, and the solid collected by filtration to obtain 66.2 of phenyl (4-cyano-3-(ethylthio)-5-isothiazolyl)carbamate, m.p. 223°–225° after recrystallization from acetic acid. The nmr spectrum was consistent with the assigned structure.

Analysis: Calc'd for $C_{13}H_{11}N_3O_2S_2$: C 51.15; H 3.63; N 13.77; Found: C 50.38; H 3.69; N 14.23.

B. 1,1-Dimethyl-3-(4-cyano-3-(ethylthio)-5-isothiazolyl)urea

Two samples (30.9 g each) of phenyl (4-cyano-3-(ethylthio)-5-isothiazolyl)carbamate were reacted with dimethylamine (9.13 g per batch) in the manner described in Example IV B. The reaction mixtures from the two runs were combined and processed as in IV B to give 41.5 g of 1,1-dimethyl-3-(4-cyano-3-(ethylthio)-5-isothiazolyl)urea, m.p. 198° after recrystallization from ethanol. The nmr spectrum was consistent with the assigned structure.

Analysis: Calc'd for $C_9H_{12}N_4OS_2$: C 42.19; H 4.72; N 21.87; Found: C 42.43; H 4.81; N 22.02.

EXAMPLE XIII

1-Methyl-3-(4-carbamoyl-3-(ethylthio-5-isothiazolyl)urea

A stirred solution of 4.0 g of 1-methyl-3-(4-cyano-3-(ethylthio)-5-isothiazolyl)urea in 6 ml of concentrated sulfuric acid was heated at 160° for 1.5 hours. After this time the reaction mixture was poured into 120 ml of ice-water, and this mixture was stirred for 45 minutes. The white precipitate was collected by filtration. The solid was recrystallized from ethanol to give 4.0 grams of 1-methyl-3-(4-carbamoyl-3-(ethylthio)-5-isothiazolyl)urea, m.p. 205°. The nmr spectra was consistent with the assigned structure.

Analysis: Calc'd for $C_8H_{12}N_4O_2S_2$: C 36.93; H 4.65; N 21.53; Found: C 37.22; H 4.80; N 21.45.

EXAMPLE XIV

1,1-Dimethyl-3-(4-cyano-3-(ethylsulfonyl)-5-isothiazolyl)urea

A stirred solution of 17 grams of 1,1-dimethyl-3-(4-cyano-3-(ethylthio-5-isothiazolyl)urea in 160 ml of acetic acid was heated to 90°. To this solution was added 4.51 g of 30% hydrogen peroxide, dropwise, at a rate sufficient to maintain the temperature of the reaction mixture at 90°. Upon completion of peroxide addition, the reaction mixture was maintained at 90°, during 3 hours. At this time thin-layer chromatography indicated the reaction mixture to contain approximately 75% ethylsulfonyl substituent and 25% ethylsulfinyl substituent. An additional 3 ml of 30% hydrogen peroxide were added and the reaction mixture was heated at 90° during an additional one hour. The reaction mixture was cooled to 5°, and a white solid was collected by filtration to give 15.2 g of 1,1-dimethyl-3-(4-cyano-3-(ethylsulfonyl)-5-isothiazolyl)-urea, m.p. 188°–189° after recrystallization from ethanol. The nmr spectrum was consistent with the assigned structure.

Analysis: Calc'd for $C_9H_{12}N_4O_3S$: C 37.51; H 4.20; N 19.44; Found: C 37.54; H 4.20; N 19.39.

EXAMPLE XV

1-Methyl-3-(4-cyano-3-(ethylsulfonyl)-5-isothiazolyl)urea

In the same manner as described in Example XIV, 15.1 g of 1-methyl-3-(4-cyano-3-(ethylthio-5-isothiazolyl)urea was reacted with 4.24 ml of 30% hydrogen peroxide in 150 ml of acetic acid to give 14.2 g of 1-methyl-3-(4-cyano-3-(ethylsulfonyl)-5-isothiazolyl)urea, m.p. 258° (decomposes) after recrystallization from dimethyl-formamide-water. The nmr and ir spectra were consistent with the assigned structure.

Analysis: Calc'd for $C_8H_{10}N_4O_3S_2$: C 35.04; H 3.68; N 20.43; Found: C 35.03; H 3.70; N 20.35.

EXAMPLE XVI

1,1-Dimethyl-3-(4-carbamoyl-3-(ethylthio)-5-isothiazolyl)urea

A mixture of 4.0 g of 1,1-dimethyl-3-(4-cyano-3-(ethylthio)-5-isothiazolyl)urea in 6 ml of concentrated sulfuric acid was heated at 100° during one hour. The reaction mixture was treated as described in Example XIII to give, after recrystallization from ethanol, 2.8 g of 1,1-dimethyl-3-(4-carbamoyl-3-(ethylthio)-5-isothiazolyl)urea, m.p. 147°. The nmr spectrum was consistent with the assigned structure.

Analysis: Calc'd for $C_9H_{14}N_4O_2S_2$: C 39.42; H 5.15; N 20.43; Found: C 39.65; H 5.15; N 20.21.

EXAMPLE XVII

1,1-Dimethyl-3-(4-cyano-3-(ethylsulfinyl)-5-isothiazolyl)urea

Seventeen grams of 1,1-dimethyl-3-(4-cyano-3-(ethylthio)5-isothiazolyl)urea was treated with 2.75 g of 30% hydrogen peroxide in the manner described in Example II. No solid separated on cooling the reaction mixture. The mixture was neutralized with saturated aqueous sodium bicarbonate solution, then concentrated to near dryness. The viscous residue was crystallized from ethanol to yield 13.8 g of 1,1-dimethyl-3-(4-cyano-3-(ethylsulfinyl)-5-isothiazolyl)urea, m.p. 162°–163°. The nmr spectrum was consistent with the assigned structure.

Analysis: Calc'd for $C_9H_{12}N_4O_2S_2$; C 39.71; H 4.44; N 20.58; Found: C 39.65; H 4.70; N 20.46.

EXAMPLE XVIII

1,1-Dimethyl-3-(4-carbamoyl-3-(ethyl-sulfonyl)-5-isothiazolyl)urea

A mixture of 9.8 g of 1,1-dimethyl-3-(4-cyano-3-(ethylsulfonyl)-5-isothiazolyl)urea and 15 ml of concentrated sulfuric acid was heated at 100° for 1.5 hours, then poured into 150 ml of ice-water. The cold mixture was stirred during one hour and the separated solid was collected by filtration. The collected solid was recrystallized twice from ethanol but thin-layer chromatography indicated an impurity to be present. The solid was subjected to column chromatography using a 250 g silica gel column. Elution was accomplished using chloroform initially and adding ethyl acetate progressively until the final solvent was a 1:1 mixture of chloroform and ethyl acetate. Progress of the elution was followed by thin-layer chromatography. The first 8 fractions were devoid of product. Fractions 9-12 contained the desired product free of impurities and fraction 13 contained traces of the impurity. Fractions 9-12 were combined and concentrated to give 2.8 g of 1,1-dimethyl-3-(4-carbamoyl-3-(ethylsulfonyl)-5-isothiaxolyl)urea, m.p. 189-190°. The nmr spectrum was consistent with the assigned structure.

Analysis:
Calc'd for $C_9H_{14}N_4O_4S_2$: C 35.30; H 4.61; N 18.30;
Found: C 35.50; H 4.73; N 18.36.

EXAMPLE XIX

1-Methyl-3-(4-carbamoyl-3-(ethylsulfonyl)-5-isothiazolyl)urea

A mixture of 8.8 g of 1-methyl-3-(4-cyano-3-(ethylsulfonyl) -5-isothiazolyl)urea and 10 ml of concentrated sulfuric acid was heated at 100° for 2.25 hours, then poured into 150 ml of ice-water. The solid was isolated and recrystallized from acetic acid-water to give 2.8 g of 1-methyl-3-(4-carbamoyl-3-(ethylsulfonyl)-5-isothiazolyl)urea, m.p. 219°-220°. An additional 2.2 g was obtained by concentrating the mother liquor from the recrystallization. The nmr and ir spectra were consistent with the assigned structure.

Analysis:
Calc'd for $C_8H_{12}N_4O_4S_2$: C 32.88; H 4.14; N 19.17;
Found: C 32.91; H 4.11; N 18.10.

EXAMPLE XX

1-Methyl-3-(4-carbamoyl-3-(ethylsulfinyl)-5-isothiazolyl)urea

A stirred suspension of 15.1 g of 1-methyl-3-(4-cyano-3-(ethylthio)-5-isothiazolyl)urea in 150 ml of acetic acid was heated to 90° and to the hot mixture was added 2.12 g of 30% hydrogen peroxide. The mixture was maintained at 90° for 3 hours. When thin-layer chromatography showed traces of unreacted ethylthio compound, an additional 10 drops of 30% hydrogen peroxide was added and the mixture was heated an additional 1.5 hours. The mixture was then cooled to 5° and the solid which separated was collected on a filter. Recrystallization from dimethylformamide-water gave 10.0 g of 1-methyl-3-(4-carbamoyl-3-(ethylsulfinyl)-5-isothiazolyl)urea; m.p. 245°. The nmr and ir spectra were consistent with the assigned structure; the ir spectrum showed no cyano absorption.

Analysis:
Calc'd for $C_8H_{12}N_4O_3S_2$: C 34.79; H 4.38; N 20.28;
Found: C 34.82; H 4.24; N 20.46.

By the procedures described above, the following compounds were obtained:

| | |
|---|---|
| Example XXI. | 1,1-Dimethyl-3-(4-cyano-3-(propylthio)-5-isothiazolyl)urea, m.p. 168-170°. |
| Example XXII. | 1-Methyl-3-(4-cyano-3-(propylthio)-5-isothiazolyl)urea, m.p. 245° (decomposes). |
| Example XXIII. | 1-Methyl-3-(4-carbamoyl-3-(propylthio)-5-isothiazolyl)urea, m.p. 189-190°. |
| Example XXIV. | 1,1-Dimethyl-3-(4-carbamoyl-3-(propylthio)-5-isothiazolyl)urea, m.p. 147-148°. |
| Example XXV. | 1-Methyl-3-(3-(butylthio)-4-cyano-5-isothiazolyl)urea, m.p. 236-237°. |
| Example XXVI. | 1-Methyl-3-(4-carbamoyl-3-(propylsulfonyl)-5-isothiazolyl)urea, m.p. 224-225°. |
| Example XXVII. | 1,1-Dimethyl-3-(4-cyano-3-(propylsulfonyl)-5-isothiazolyl)urea, m.p. 162-165°. |
| Example XXVIII. | 1,1-Dimethyl-3-(4-carbamoyl-3-(propylsulfonyl)-5-isothiazolyl)urea, m.p. 154-156°. |
| Example XXIX. | 1-Methyl-3-(3-(allylthio)-4-cyano-5-isothiazolyl)urea, m.p. 225-227°. |
| Example XXX. | 1-Methyl-3-(3-(benzylthio)-4-cyano-5-isothiazolyl)urea, m.p. 248°. |
| Example XXXI. | 1-Methyl-3-(4-carbamoyl-3-(isopropylthio)-5-isothiazolyl)urea, m.p. 166-168°. |
| Example XXXII. | 1-Methyl-3-(4-cyano-3-(isopropylthio)-5-isothiazolyl)urea, m.p. 228-230°. |
| Example XXXIII. | 1,1-Dimethyl-3-(4-cyano-3-(propylsulfinyl)-5-isothiazolyl)urea, m.p. 158-160°. |

The herbicidal activities of the compounds of this invention were demonstrated as follows. In preemergence tests, rows of seeds of lima beans (*Phaseolus lunatus*), corn (*Zea mays*), wild oats (*Avena fatua*), lettuce (*Lactuca sativa*), mustard (*Brassica juncea*) and crabgrass (*Digitaria sanguinalis*) were planted in shallow flat-bed trays (20 cm. × 15 cm. × 7.5 cm.) containing 5 cm. to 7.5 cm. of sandy loam soil. Within 24 hours after planting, an aqueous acetone solution of the compound (using sufficient acetone to obtain solution) was sprayed on the soil at a rate equivalent to 8.96 kilograms per hectare, using a total volume equivalent to 760 liters per hectare. The trays were maintained under normal growing conditions in the greenhouse for about 3 weeks, after which the herbicidal efficacy of the compound was assessed. Individual plant species were examined in comparison with untreated plants. Table 1 lists data collected in preemergence tests with compounds of the present invention.

In postemergence tests, rows of seeds were planted as for preemergence tests and the untreated flats were maintained in the greenhouse until the first trifoliate leaves of the bean plants were unfolding. The test plants were then sprayed with an aqueous acetone solution of the compound as for preemergence tests. The plants were returned to the greenhouse and held under normal growing conditions for about 3 more weeks, after which the herbicidal efficacy of the compound was assessed. Table 2 lists data collected in postemergence tests with compounds of the present invention.

Table 1
Preemergence Herbicidal Activity of
3-(Substituted thio)isothiazolylureas and -alkanamides
(expressed as % kill at 8.96 kg/hectare)

| Compound of Example | Lima Bean | Corn | Wild Oats | Lettuce | Mustard | Crabgrass |
|---|---|---|---|---|---|---|
| I | 25 | 0 | 0 | 100 | 100 | 0 |
| II | 100 | 0 | 20 | 100 | 80 | 0 |
| III | 100 | 100 | 100 | 100 | 100 | 100 |
| IV | 100 | 0 | 0 | 30 | 40 | 0 |
| V | 100 | 0 | 100 | 100 | 50 | 0 |
| VI | 100 | 0 | 100 | 100 | 50 | 0 |
| VII | 00 | 100 | 100 | 100 | 100 | 100 |
| VIII | 100 | 30 | 100 | 100 | 100 | 100 |
| IX | 100 | 0 | 40 | 100 | 100 | 0 |
| X(A) | 50 | 0 | 0 | 100 | 30 | 0 |
| X(V) | 100 | 0 | 10 | 20 | 30 | 20 |
| XI | 30 | 0 | 0 | 90 | 100 | 0 |
| XII | 100 | 0 | 40 | 100 | 100 | 30 |
| XIII | 100 | 100 | 100 | 100 | 100 | 100 |
| XIV | 100 | 0 | 10 | 100 | 40 | 0 |
| XV | 100 | 0 | 50 | 100 | 100 | 0 |
| XVI | 100 | 100 | 100 | 100 | 100 | 100 |
| XVII | 100 | 0 | 0 | 25 | 0 | 0 |
| XVIII | 100 | 70 | 100 | 100 | 100 | 100 |
| XIX | 100 | 100 | 100 | 100 | 100 | 100 |
| XX | 100 | 30 | 100 | 90 | 80 | 70 |
| XXI | 40 | 0 | 10 | 50 | 80 | 0 |
| XXII | 50 | 0 | 0 | 50 | 100 | 0 |
| XXIII | 100 | 100 | 100 | 100 | 100 | 100 |
| XXIV | 100 | 0 | 80 | 100 | 100 | 100 |
| XXV | 0 | 0 | 0 | 10 | 20 | 0 |
| XXVI | 100 | 100 | 100 | 100 | 100 | 100 |
| XXVII | 0 | 0 | 0 | 70 | 80 | 0 |
| XXVIII | 100 | 70 | 100 | 30 | 100 | 100 |

Table 1-continued

Preemergence Herbicidal Activity of
3-(Substituted thio)isothiazolylureas and -alkanamides
(expressed as % kill at 8.96 kg/hectare)

| Compound of Example | Lima Bean | Corn | Wild Oats | Lettuce | Mustard | Crabgrass |
|---|---|---|---|---|---|---|
| XXIX | 0 | 0 | 0 | 0 | 0 | 0 |
| XXX | 0 | 0 | 0 | 0 | 0 | 0 |
| XXXI | 100 | 100 | 100 | 100 | 100 | 100 |
| XXXII | 100 | 70 | 100 | 100 | 100 | 50 |
| XXXIII | 0 | 0 | 0 | 0 | 0 | 0 |

Table 2

Postemergence Herbicidal Activity of
3-(Substituted thio)isothiazolylureas and -alkanamides
(expressed as % kill at 8.96 kg/hectare)

| Compound of Example | Lima Bean | Corn | Wild Oats | Lettuce | Mustard | Crabgrass |
|---|---|---|---|---|---|---|
| I | 0 | 0 | 0 | 100 | 100 | 0 |
| II | 0 | 0 | 0 | 100 | 100 | 0 |
| III | 100 | 100 | 100 | 100 | 100 | 100 |
| IV | 100 | 0 | 0 | 80 | 100 | 0 |
| V | 100 | 0 | 100 | 100 | 100 | 0 |
| VI | 100 | 0 | 30 | 100 | 100 | 0 |
| VII | 100 | 100 | 100 | 100 | 100 | 100 |
| VIII | 100 | 70 | 100 | 100 | 100 | 100 |
| IX | 100 | 0 | 50 | 100 | 100 | 30 |
| X(A) | 25 | 0 | 0 | 100 | 100 | 0 |
| X(B) | 100 | 0 | 20 | 100 | 100 | 70 |
| XI | 100 | 0 | 0 | 100 | 100 | 0 |
| XII | 100 | 0 | 40 | 100 | 100 | 30 |
| XIII | 100 | 100 | 100 | 100 | 100 | 100 |
| XIV | 100 | 0 | 20 | 100 | 100 | 100 |
| XV | 100 | 0 | 10 | 100 | 100 | 90 |
| XVI | 100 | 100 | 100 | 100 | 100 | 100 |
| XVII | 100 | 0 | 20 | 100 | 100 | 80 |
| XVIII | 100 | 100 | 100 | 100 | 100 | 100 |
| XIX | 100 | 100 | 100 | 100 | 100 | 100 |
| XX | 100 | 0 | 100 | 100 | 100 | 100 |
| XXI | 0 | 0 | 0 | 100 | 100 | 0 |
| XXII | 60 | 0 | 30 | 100 | 100 | 0 |
| XXIII | 100 | 100 | 100 | 100 | 100 | 70 |
| XXIV | 100 | 0 | 100 | 100 | 100 | 70 |
| XXV | 30 | 0 | 20 | 0 | 30 | 10 |
| XXVI | 100 | 100 | 100 | 100 | 100 | 100 |
| XXVII | 100 | 0 | 0 | 100 | 100 | 0 |
| XXVIII | 100 | 70 | 100 | 100 | 100 | 100 |
| XXIX | 0 | 0 | 0 | 100 | 100 | 0 |
| XXX | 100 | 0 | 100 | 100 | 100 | 20 |
| XXXI | 100 | 100 | 100 | 100 | 100 | 100 |
| XXXII | 100 | 100 | 100 | 100 | 100 | 100 |
| XXXIII | 0 | 0 | 0 | 100 | 80 | 0 |

For herbicidal application, the compounds of this invention may be utilized in diverse formulations including the agricultural adjuvants and agricultural carriers, i.e. those materials normally employed to facilitate the dispersion of active ingredients in agricultural applications, recognizing the fact that the formulation and mode of application of a toxicant may affect the activity of the material in a given application. Thus, a compound of this invention may be formulated as a granule of relatively large particle size, as a wettable powder, as an emulsifiable concentrate, as a solution, or as any of several other known types of formulations, depending on the desired mode of application.

Granular formulations are particularly useful for aerial distribution or for penetration of a canopy of foliage. Useful granular formulations may be of several types. Impregnated granules are those wherein the active ingredient is applied to large particles of an absorbent carrier, such as an attapulgite or kaolin clay, corncobs, expanded mica, etc., normally in the form of a solution in a solvent. Surface-coated granules may be produced by spraying the molten active ingredient onto the surface of a generally nonabsorbent particle or by spraying on a solution of active ingredient in a solvent. The core may be water-soluble such as a prilled fertilizer, or insoluble such as sand, marble chips or coarse talc. Particularly useful is a granule wherein a wettable powder is applied as a surface coating to a sand or other insoluble particle such that the wettable powder may be dispersed on contact of the granule with moisture. Granules may be produced by agglomeration of dusts or powders by compaction rollers, by extrusion through a die or by use of granulating disc. Granular formulations may vary widely in concentration, with useful formulations containing as little as 0.5% or as much as 95% of active ingredient.

Wettable powders, also useful formulations for both pre- and postemergence herbicides, are in the form of finely divided particles which disperse readily in water or other dispersants. The wettable powder is ultimately applied to the soil or to the undesired plant growth either as a finely divided dry material or as an emulsion in water or other liquid. Typical carriers for wettable powders include fuller's earth, kaolin clays, silicas and other highly absorbent, readily wet inorganic diluents. Wettable powders normally are prepared to contain about 5% to 8% of active ingredient, depending on the absorbency of the carrier, and usually also contain a small amount of a wetting, dispersing or emulsifying agent to facilitate dispersion. For example, a useful wettable powder formulation contains 80.8 parts of 1-methyl-3-(4-carbamoyl-3-(methylsulfonyl)-5-isothiazolyl)urea, 17.9 parts of palmetto clay, and 1.0 part of sodium lignosulfonate and 0.3 part of sulfonated aliphatic polyester as wetting agents.

Other useful formulations for herbicidal applications are the emulsifiable concentrates, which are homogeneous liquid or past compositions dispersible in water or other dispersant, and may consist entirely of a compound of this invention with liquid or solid emulsifying agent, or may also contain an agriculturally acceptable liquid carrier, such as xylene, heavy aromatic naphthas, isophorone and other nonvolatile organic solvents.

Typical wetting, dispersing or emulsifying agents used in agricultural formulations include, for example, the alkyl and alkylaryl sulfonates and sulfates and their sodium salts; polyethylene oxides; sulfonated oils, fatty acid esters of polyhydric alcohols; and other types of surface-active agent, many of which are available in commerce. The surface-active agent, when used, normally comprises from 1% to 15% by weight of the herbicidal composition.

These formulations may be applied without further dilution or as dilute solutions, emulsions or suspensions in water or other suitable diluent. The compositions may be applied to the area wherein control is desired by spraying onto the undesired vegetation or onto the surface of the soil in the case of liquid compositions or by distribution from mechanical equipment in the case of solids. The surface-applied material may also be blended into the upper layer of soil by cultivation, or left as applied, as is appropriate to gain the optimum results with the particular treatment.

The active herbicidal compounds of this invention may be formulated and/or applied with insecticides, fungicides, namaticides, plant-growth regulators, fertilizers, and other agricultural chemicals. In applying the active compounds of this invention, whether formulated alone or with other agricultural chemicals, an effective amount and concentration of isothiazolylurea are of course employed.

It is apparent that various modifications may be made in the formulation and application of the novel compounds of this invention, without departing from the inventive concept herein, as defined in the following claims:

I claim:

1. A substituted isothiazole of the formula:

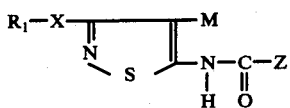

wherein $R_1$ is alkyl or alkenyl of up to six carbon atoms;

Z is $-NR_2R_3$ or $R_4$ in which $R_2$ is methyl, $R_3$ is methyl or hydrogen, and $R_4$ is alkyl of one to six carbon atoms;

M is cyano or carbamoyl; and X is ——, —SO—, or —SO$_2$—.

2. A compound of claim 1 in which $R_1$ is alkyl of 1 to 4 carbons, $R_2$ is methyl, and $R_3$ is methyl or hydrogen.

3. A compound of claim 2 in which M is cyano.

4. The compound of claim 3 which is 1-methyl-3-(4-cyano-3-(methylthio)-5-isothiazolyl)urea.

5. A compound of claim 2 in which M is carbamoyl.

6. A compound of claim 5 in which $R_3$ is hydrogen.

7. The compound of claim 6 which is 1-methyl-3-(4-carbamoyl-3-(methylthio)-5-isothiazolyl)urea.

8. The compound of claim 6 which is 1-methyl-3-(4-carbamoyl-3-(methylsulfinyl)-5-isothiazolyl)urea.

9. The compound of claim 6 which is 1-methyl-3-(4-carbamoyl-3-(methylsulfonyl)-5-isothiazolyl)urea.

10. The compound of claim 6 which is 1-methyl-3-(4-carbamoyl-3-(ethylthio)-5-isothiazolyl)urea.

11. The compound of claim 6 which is 1-methyl-3-(4-carbamoyl-3-(ethylsulfinyl)-5-isothiazolyl)urea.

12. The compound of claim 6 which is 1-methyl-3-(4-carbamoyl-3-(ethylsulfonyl)-5-isothiazolyl)urea.

13. The compound of claim 6 which is 1-methyl-3-(4-carbamoyl-3-(propylthio)-5-isothiazolyl)urea.

14. The compound of claim 6 which is 1-methyl-3-(4-carbamoyl-3-(propylsulfonyl)-5-isothiazolyl)urea.

15. A compound of claim 5 in which $R_3$ is methyl.

16. The compound of claim 15 which is 1,1-dimethyl-3-(4-carbamoyl-3-(ethylthio)-5-isothiazolyl)urea.

17. The compound of claim 15 which is 1,1-dimethyl-3-(4-carbamoyl-3-(ethylsulfonyl)-5-isothiazolyl)urea.

18. A herbicidal composition comprising an herbicidally effective amount of a compound of claim 1 in admixture with an extender.

19. A method of preventing and destroying undesired plant growth which comprises applying to the locus to be protected an herbicidally effective amount of a compound of claim 1.

UNITED STATES PATENT AND TRADEMARK OFFICE
CERTIFICATE OF CORRECTION

PATENT NO. : 4,057,416

DATED : November 8, 1977

INVENTOR(S) : L. K. Gibbons

It is certified that error appears in the above—identified patent and that said Letters Patent is hereby corrected as shown below:

Column 7, line 28, "-2,2-dimethyl- pro-" should read
-- -2,2-dimethylpro- --; line 45, "2-cyano-3,3-bio(ethylthio)"
should read --2-cyano-3,3-bis(ethylthio)--; line 46, "di(sodi-
omercapto)- me-" should read --di(sodiomercapto)me- --.
Column 9, line 54 "cyano-3-(ethylthio-5-isothiazolyl)urea"
should read --cyano-3-(ethylthio)-5-isothiazolyl)urea--.
Column 11, line 5, "(4-carbamoyl-3-(ethylsulfonyl)-5-isothi-
axolyl)urea," should read --(4-carbamoyl-3-(ethylsulfonyl)-5-
isothiazolyl)urea,--. Column 12, line 53, "VII 00" should read
--VII 100--. Column 15, line 20, "X is ---," should read
--X is -S- --.

Signed and Sealed this

Eighteenth Day of November 1980

[SEAL]

Attest:

SIDNEY A. DIAMOND

Attesting Officer

Commissioner of Patents and Trademarks